US007014865B1

(12) United States Patent
Buchholz et al.

(10) Patent No.: US 7,014,865 B1
(45) Date of Patent: Mar. 21, 2006

(54) NATURAL FORMULATION FOR THE TREATMENT AND PREVENTION OF DEPRESSION, CONTAINING ST. JOHN'S WORT AND DERIVATIVES OF DIHYDRO- AND TETRAHYDROFOLIC ACID

(75) Inventors: Herwig Buchholz, Frankfurt (DE); Angela Dudda, Frankfurt (DE); Jerzy Meduski, Playa Del Rey, CA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/807,401

(22) PCT Filed: Oct. 8, 1999

(86) PCT No.: PCT/EP99/07556

§ 371 (c)(1),
(2), (4) Date: Apr. 13, 2001

(87) PCT Pub. No.: WO00/23089

PCT Pub. Date: Apr. 27, 2000

Related U.S. Application Data

(60) Provisional application No. 60/104,710, filed on Oct. 19, 1998.

(30) Foreign Application Priority Data

Oct. 19, 1998 (US) .............................. 60/104,710

(51) Int. Cl.
*A61K 9/00* (2006.01)
*A61K 9/48* (2006.01)
*A61K 35/00* (2006.01)
*A61K 35/78* (2006.01)

(52) U.S. Cl. ...................... 424/456; 424/400; 424/439; 424/464; 424/484; 424/489; 424/451; 424/725; 424/730

(58) Field of Classification Search ................ 424/400, 424/439, 464, 484, 489, 451, 456, 725, 730
See application file for complete search history.

(56) References Cited

U.S. PATENT DOCUMENTS 5,820,867 A * 10/1998 Bewicke ..................... 424/730
6,068,846 A * 5/2000 Cho et al. ................... 424/730
6,254,904 B1 7/2001 Bailey
6,297,224 B1 10/2001 Allen et al.

FOREIGN PATENT DOCUMENTS

WO          9937155          7/1999

* cited by examiner

*Primary Examiner*—Thurman K. Page
(74) *Attorney, Agent, or Firm*—Millen, White, Zelano & Branigan, P.C.

(57) ABSTRACT

The present invention relates to novel compositions containing a combination of the plant St. John's Wort (*Hypericum perforatum* L.), its extracts of active ingredients and derivatives of dihydro- and tetrahydrofolic acid. This natural formulation is useful for the treatment and prevention of depression with a better effect than the ingredient compounds alone.

12 Claims, 1 Drawing Sheet

Folic acid
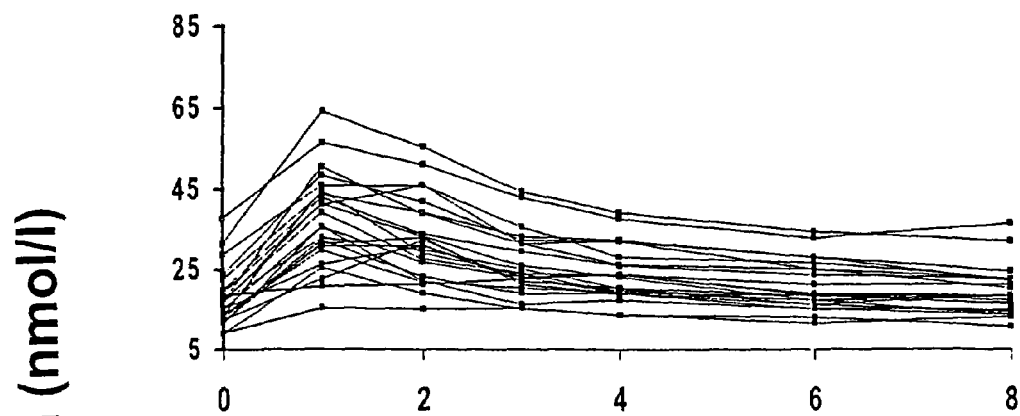
Metafolin™
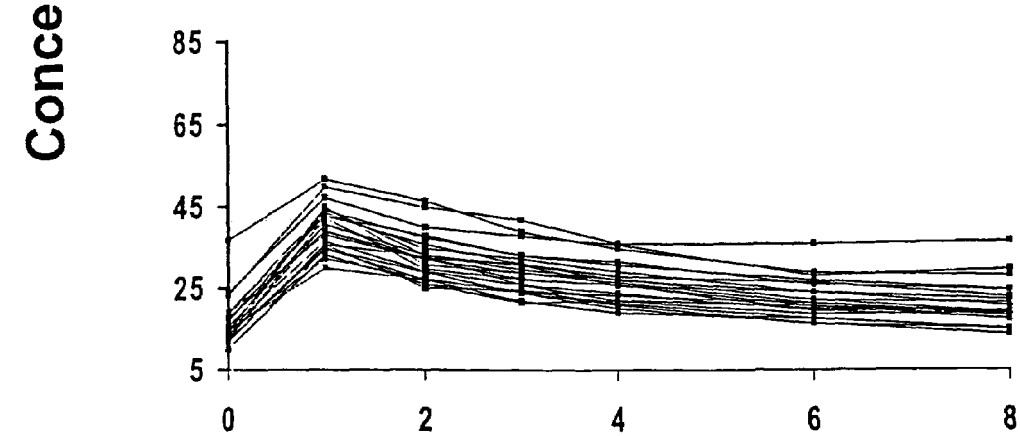
Intervention Time (hour)

NATURAL FORMULATION FOR THE TREATMENT AND PREVENTION OF DEPRESSION, CONTAINING ST. JOHN'S WORT AND DERIVATIVES OF DIHYDRO- AND TETRAHYDROFOLIC ACID

This application claims the benefit of priority from U.S. Provisional Application 60/104,710, filed Oct. 19, 1998.

The present invention relates to novel compositions containing a combination of the plant St. John's Wort (*Hypericum perforatum* L.) and derivatives of folic acid. This natural formulation is useful for the treatment and prevention of depression with a better effect than the ingredient compounds alone.

Depression is an increasingly common psychiatric disorder, affecting a large part of the population, especially in developed countries. The etiology and precise mechanisms of depressive disorders are not completely understood, but are believed to involve the decrease of certain neutrotransmitters, particularly serotonin (5-HT) and its metabolite, 5-hydroxyindole acetic acid (5-HIAA) in the central nervous system. High level of homocysteine and both folate and vitamin B12 deficiency are also linked to the etiology of depression.

Modern standard pharmacological antidepression agents can be divided into several major groups: selective serotonin reuptake inhibitors, tricyclic and other heterocyclic antidepressants, monoamine oxidase (MAO) inhibitors, etc. All of them provoke a wide range of adverse effects—from undesirable psychostimulation to hypertension and cardiotoxicity.

Despite some progress in this area and the availability of new antidepressants with fewer side effects, this direction of research has not granted a safe and efficient way to treat depression.

Therefore, there is a need for an innovative formulation based on the natural metabolites useful for the prevention and treatment of depression.

Now it has been found that the combination of natural compounds—St. John's Wort or its extracts or active ingredients and folic acid derivatives—constitutes a unique safe multifaceted approach to the prevention and treatment of mild to moderate forms of depression.

St. John's Wort is a perennial flowering plant that has been traditionally used in folk medicine for thousands of years due to its anti-inflammatory, analgesic and sedative properties, particularly for wound healing and treatment of respiratory infections (see Miller, A. L., 1998, Altern. Med. Rev. 3, 1, 18–26).

Recently it attracted attention as an effective agent for the treatment of mild to moderate depression and also of the seasonal affective disorder. Other indications include psychovegetative dysfunctions, anxiety, nervous restlessness and similar disorders. About 30 clinical studies confirmed that the efficacy of St. John's Wort (SJW) is compared to popular synthetic antidepression agents (amitriptyline, imipramine, maprotiline, etc.) without any side effects (see Lieberman, S., 1998, Altern. Complement. Therapies, June, 163–168). It did not lead to the impairment of attention, concentration or reaction. The only side effect mentioned in the literature is the reversible increased photosensitivity to UV light after prolonged use of the St. John's Wort extract (see Golsch, S. et al., 1997, Hautarzt 48, 4, 249–252). No negative drug interaction associated with St. John's Wort is reported.

The mechanism of action of SJW is not completely defined. In its extract there could be identified eight secondary metabolites so far amentoflavone, biapigenin, hyperforin, hypericin, hyperosid, pseudohypericin, quercetin and rutin (see Buter, B. et al., 1998, Planta Med. 64, 5, 431–437).

There are indications that hypericin, one active compound from SJW is a strong inhibitor of catechol-O-methyltransferase (see Mueller, W. E. G. et al., 1994, J. Geriatr. Psychiatr. Neurol. 7(Suppl. 1), 63–64; Mueller, W. E. G., 1995, Wissenschaftlicher Bericht, Lichtwer Pharma GmbH, Berlin) and monoamine oxidases (see Suzuki, O. et al., 1984, Planta Med. 50, 272–274). Monoamine oxidases participate in the breakdown of neurotransmitters serotonin and noradrenalin (see Perovic, S. et al., 1995, Arzn. Forsch/Drug Res. 45, 1145–1148).

Further effects include the modulation of the serotonin receptors or/and a general influence of hypericum extracts on central dopaminerge neurons (see Butterweck, V. et al., 1998, Planta Med. 64, 4, 291–294).

Other reports suggest that since pure hypericin shows no inhibiting effect on MAO (see Bladt, S. et al., 1994, J. Geriatr. Psychiatr. Neurol. 7, Suppl. 1, 57–59), the antidepressive effect of SJW cannot be explained in terms of MAO inhibition. In a series of recent publications it has been demonstrated that hyperforin, a major lipophilic non-nitrogenous constituent of SJW (and of Hyperici Oleum), is also a potent inhibitor of uptake of serotonin, dopamine, noradrenaline, GABA, and L-glutamate in vitro (see Chattarjee, S. S. et al., 1998, Life Sci. 63, 6, 499–510).

Most of the known pharmacological properties of the SJW extract can also be demonstrated with pure hyperforin. Therefore it has been suggested that hyperforin could be a major active principle of the plant (see Laakmann, G. et al., 1998, Pharmacopsychiatry 31, Suppl. 1, 54–59). Most researchers agree that the combination of low-grade monoamino oxidase inhibition and noradrenaline and serotonin re-uptake blocade seems to be the most likely mechanism of action of SJW (see Nordfors, M. et al., 1997, Lakartidningen 94, 25, 2365–2367).

A close relationship between folate metabolism and depression is well documented (see Alpert, J. E. et al., 1997, Nutrition Reviews 55, 5, 145–149). It is known that depressive symptoms are the most common indicator of folate deficiency. Depressed patients have been consistently found to have lower serum folate concentrations than control subjects (see Fava, M. et al., 1997, Am. J. Psychiatry 154, 426–428). Recently, low folate levels were linked to the poor response to selective serotonin uptake inhibitors.

The biochemical mechanisms by which folic acid derivatives affect the neuropsychiatric status apparently involve transmethylation reactions with components (DNA, RNA, proteins, biomembranes) of the central nervous system. The methyl group from folate (in the form of active metabolite 5-methyltetrahydrofolic acid, 5-MTHF, or 5-formyltetrahydrofolic acid, after being reduced to 5-MTHF) is transferred to homocysteine to form methionine. The de novo synthesis of methionine requires vitamin B12, since it involves a reaction catalyzed by vitamin B12-dependent methionine synthetase. Methionine then participates in the reaction producing S-adenosylmethionine which is an important intermediate in more than 35 transmethylation reactions in CNS (see Bottiglieri, T. et al., 1994, Drugs 48, 137–152). Among reactions relevant to the effect of folate level on depression is the synthesis of tetrahydrobiopterin, a cofactor in the hydroxylation of phenylalanine and tryptophan playing a crucial role in the biosynthesis of the neurotransmitters dopamine, norepinephrine and serotonin.

The significant beneficial impact of the suggested composition on psychoneurological status is expected through a reduction of high levels of homocysteine in the brain due to 5-methyl-tetrahydrofolic acid treatment. High levels of homocysteine have been recognized as a major risk factor for a wide range of diseases including neurological and cerebrovascular diseases. In particular, increased plasma homocysteine level has been linked to depression, mental and severe psychomotoric retardation.

Among major causes of hyperhomocysteinemia are genetic deficiencies of methylenetetrahydrofolate reductase (MTHFR) or cystathionine β-synthase (CS), key enzymes in the metabolism of folic acid. Methylenetetrahydrofolate reductase deficiency is a relatively common disorder, and about 15% of the general population have abnormal MTHFR genotype. A successful treatment of hyperhomocysteinemia with folic acid and cofactors of folic acid metabolism (e.g. vitamin B6 and vitamin B12) has been documented in numerous studies (see Bottiglieri, T., 1996, Nutrition Reviews 54, 12, 382–390).

The active metabolite in the folic acid pathway is 5-methyltetrahydrofolic acid which, orally administered, should be more efficacious than folic acid. Folic acid given to the patients has to go through several reactions including a MTHFR catalyzed reaction to produce 5-methyltetrahydrofolic acid. All these steps can be by-passed with the direct introduction of 5-methyltetrahydrofolic acid. Of major importance is that 5-methyltetrahydrofolic acid is the only metabolite which is able to pass the blood-brain barrier. However, because of the possible conversion of other folic acid derivatives to 5-methyltetrahydrofolic acid, it is certainly possible to use for example 5-formyltetrahydrofolic acid, 10-formyltetrahydrofolic acid, 5,10-methylentetrahydrofolic acid, 5-methenyltetrahydrofolic acid, tetrahydrofolic acid, dihydrofolic acid and folic acid itself.

Surprisingly it has been found that St. John's Wort, a traditional soft antidepressant which improves the psychovegetative conditions by modulating the action of neurotransmitters, and 5-methyltetrahydrofolic acid which improves the psychiatric condition by a reduction of the homocysteine concentration in the brain augment their beneficial effect when used in combination. As the results of their synergistic effect, symptoms of depression are removed and also metabolic conditions of the central nervous system are improved. This leads to a decrease of intensity and frequency of attacks of depression.

Therefore, the object of the present invention is an orally applicable natural formulation comprising St. John's Wort (*Hypericum perforatum*) or its extracts or active ingredients in combination with folic acid derivatives or suitable salts thereof.

These natural formulations are highly useful for the prevention and the therapy of depression.

The St. John's Wort may be used as the whole plant, its water extract, alcohol, ethanol, or any other extract. It is also possible to use just one or more of the plants ingredients. Especially preferred is the hypericin which is commercially available in different concentrations (e.g. 0.3% Hypericin St. John's Wort, Fa. Lichtwer, Berlin).

As the second ingredient folic acid derivatives selected from the group consisting of 5-methyltetrahydrofolic acid, tetrahydrofolic acid, dihydrofolic acid, 5-formyltetrahydrofolic acid, 10-formyltetrahydrofolic acid, 5,10-methylentetrahydrofolic acid, and 5-methenyltetrahydrofolic acid or their suitable salts are used.

5-methyltetrahydrofolic acid or 5-formyltetrahydrofolic acid are especially preferred.

The folic acid derivatives may also be in the form of their salts. Preferred are suitable salts like their sodium or calcium salts.

In the case of application of 5-formyltetrahydrofolic acid, additional ingredients should be vitamin B12 and betaine anhydrous. Betaine is a donor for methyl groups which are transferred by vitamin B12 to homocysteine.

Useful compositions may contain in one serving 400 to 5 000 mcg of folic acid derivative and in case of 5-formyltetrahydrofolic acid 50 mg to 1 000 mg betaine and 0,5 to 10 mcg vitamin B12. The dose of St. John's Wort can be adjusted to the particular case in a wide range. Preferably a commercially available extract of 0.3% Hypericin is applied in an amount of 100 mg to 1000 mg.

The formulations according to the present invention may be prepared in form of tablets, gelcaps, capsules or syrups.

The compositions of the present invention preferably are useful as food supplements, but they may also be administered in a pharmaceutical treatment.

The present invention makes available:
a) a method of prevention of neurological and psychopathological diseases;
b) a method of supporting a pharmacological treatment of neurological and psychopathological diseases;
c) a method leading to a decrease of intensity and frequency of attacks of depression;
d) a natural approach without any side effects for the prevention and treatment of depression;

by oral administration of a formulation described above and/or related and suggested above modifications of this composition.

Thus, this invention provides an innovative formulation based on natural ingredients useful for the prevention and treatment of depression. The combination of the natural compounds—St. John's Wort or its extracts or active ingredients and derivatives of dihydro- and tetrahydrofolic acid, derivatives thereof or corresponding salts—constitutes a unique and safe approach to the prevention and treatment of mild to moderate forms of depression without any side effects.

The entire disclosure of all applications, patents and publications, cited above and below are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

EXAMPLES

Example 1

A lower dosed formulation according to the invention is obtained by mixing the following components:
300 mg of 0.3% Hypericin St. John's Wort (Fa. Lichtwer, Berlin) and
400 mcg of 5-methyltetrahydrofolic acid calcium salt, formulated in gelcaps.

Example 2

A higher dosed formulation is obtained by mixing
600 mg of 0.3% Hypericin St. John's Wort and
800 mcg of 5-methyltetrahydrofolic acid calcium salt, formulated in gelcaps.

Example 3

A formulation according to the invention is obtained by mixing
300 mg of 0.3% Hypericin St. John's Wort,
400 mcg of 5-formyltetrahydrofolic acid calcium salt,
300 mg betaine anhydrous and
3 mcg vitamin B12 (cyanocobalamin), formulated in gelcaps.

Example 4

A higher dosed formulation is obtained by mixing
600 mg of 0.3% Hypericin St. John's Wort,
800 mcg of 5-formyltetrahydrofolic acid calcium salt,
600 mg betaine anhydrous and
6 mcg vitamin B12 (cyanocobalamin), formulated in gelcaps.

The invention claimed is:

1. An orally applicable natural formulation comprising St. John's Wort (*Hypericum perforatum*) or an extract or active ingredient thereof, and 400 to 5000 mcg of a calcium or sodium salt of 5-formyltetrahydrofolic acid; wherein said formulation is in the form of a gelcap.

2. A formulation according to claim 1 comprising a water extract or alcohol extract of Hypericin St. John's Wort.

3. A formulation according to claim 1 comprising a water extract or ethanol extract of Hypericin St. John's Wort.

4. A formulation according to claim 1 which comprises additionally vitamin B12 and betaine anhydrous.

5. A formulation according to claim 4 in the form of a dosage unit, comprising 400 to 5000 mcg of a calcium or sodium salt of 5-formyltetrahydrofolic acid, 50 mg to 2000 mg of betaine anhydrous and 0.5 to 10 mcg of vitamin B12.

6. A food supplement comprising a formulation of claim 1.

7. A method of preventing a neurological or a psychopathological disease which comprises orally administering to a patient in need thereof a therapeutically effective amount of a formulation according to claim 1.

8. A method of supporting a pharmacological treatment of a neurological or a psychopathological disease which comprises orally administering to a patient in need thereof a therapeutically effective amount of a formulation according to claim 1.

9. A method of preventing a neurological or a psychopathological disease which comprises orally administering to a patient in need thereof a therapeutically effective amount of a formulation according to claim 4.

10. A method of supporting a pharmacological treatment of a neurological or a psychopathological disease which comprises orally administering to a patient in need thereof a therapeutically effective amount of a formulation according to claim 4.

11. A method of preventing a neurological or a psychopathological disease which comprises orally administering to a patient in need thereof a therapeutically effective amount of a formulation according to claim 5.

12. A method of supporting a pharmacological treatment of a neurological or a psychopathological disease which comprises orally administering to a patient in need thereof a therapeutically effective amount of a formulation according to claim 5.

* * * * *

UNITED STATES PATENT AND TRADEMARK OFFICE
CERTIFICATE OF CORRECTION

| | | |
|---|---|---|
| PATENT NO. | : 7,014,865 B1 | Page 1 of 1 |
| APPLICATION NO. | : 09/807401 | |
| DATED | : March 21, 2006 | |
| INVENTOR(S) | : Herwig Buchholz et al. | |

It is certified that error appears in the above-identified patent and that said Letters Patent is hereby corrected as shown below:

Column 6, line 5 claim 6 reads "A method of preventing" should read -- A method of treating --
Column 6, line 14 claim 9 reads "A method of preventing" should read -- A method of treating --
Column 6, line 23 claim 11 reads "A method of preventing" should read -- A method of treating --

Signed and Sealed this

Ninth Day of September, 2008

JON W. DUDAS
*Director of the United States Patent and Trademark Office*